United States Patent
Yoshizawa et al.

(10) Patent No.: US 8,227,430 B2
(45) Date of Patent: Jul. 24, 2012

(54) INJECTABLE, INJECTION SOLUTION, AND INJECTION KIT PREPARATION

(75) Inventors: Teruhisa Yoshizawa, Yokohama (JP); Akiko Miyoshi, Chuo-ku (JP); Masato Ota, Yokohama (JP)

(73) Assignee: Meiji Seika Pharma Co., Ltd, Tokyo (JP)

( * ) Notice: Subject to any disclaimer, the term of this patent is extended or adjusted under 35 U.S.C. 154(b) by 185 days.

(21) Appl. No.: 12/676,291

(22) PCT Filed: Sep. 3, 2008

(86) PCT No.: PCT/JP2008/065865
§ 371 (c)(1),
(2), (4) Date: Mar. 3, 2010

(87) PCT Pub. No.: WO2009/031577
PCT Pub. Date: Mar. 12, 2009

(65) Prior Publication Data
US 2010/0173862 A1    Jul. 8, 2010

(30) Foreign Application Priority Data
Sep. 4, 2007  (JP) ................. 2007-228516

(51) Int. Cl.
*A61K 31/70* (2006.01)

(52) U.S. Cl. ............................................. 514/34
(58) Field of Classification Search .............. 514/34
See application file for complete search history.

(56) References Cited

U.S. PATENT DOCUMENTS

| | | | |
|---|---|---|---|
| 4,675,311 A | 6/1987 | Gatti et al. | |
| 4,840,938 A | 6/1989 | Gatti et al. | |
| 5,091,372 A | 2/1992 | Gatti et al. | |
| 5,091,373 A | 2/1992 | Gatti et al. | |

FOREIGN PATENT DOCUMENTS

| | | |
|---|---|---|
| JP | 58-105917 A | 6/1983 |
| JP | 61-246129 A | 11/1986 |
| JP | 2919112 B2 | 11/1992 |
| JP | 07-076515 A | 3/1995 |
| JP | 09-124503 A | 5/1997 |
| JP | 2000-212088 A | 8/2000 |
| JP | 2003-261449 A | 9/2003 |
| JP | 2004-51526 A | 5/2004 |
| WO | 02/47661 A1 | 6/2002 |

OTHER PUBLICATIONS

Q and A of injection drug incompatability, Jiho Inc., 2006, pp. 61-62.
International Search Report of PCT/JP2008/065865 dated Oct. 7, 2008.

*Primary Examiner* — Elli Peselev
(74) *Attorney, Agent, or Firm* — Sughrue Mion, PLLC

(57) ABSTRACT

Provided is an injectable comprising: an anthracycline antineoplastic antibiotic; and at least one acid amide selected from the group consisting of nicotinic acid amide, isonicotinic acid amide and gentisic acid ethanolamide.

6 Claims, No Drawings

INJECTABLE, INJECTION SOLUTION, AND INJECTION KIT PREPARATION

The present application is a national stage application under 35 U.S.C. §371 of PCT/JP2008/065865 filed Sep. 3, 2008, which in turn claims priority to JP 2007-228516 filed Sep. 4, 2007; all of which are incorporated herein by reference.

TECHNICAL FIELD

The present invention relates to a readily soluble injectable with an improved solubility of an anthracycline antineoplastic antibiotic, as well as an injection solution and an injection kit preparation using the same.

BACKGROUND OF THE INVENTION

An anthracycline antineoplastic antibiotic is a potent anticancer antibiotic, and is widely used for treatment of a malignant lymphoma, leukemia, breast cancer, and the like. In many cases, the antibiotic is administered to the patient in the form of, generally, an injectable (injection solution).

Although the injectable of the anthracycline antineoplastic antibiotic can be dissolved in distilled water for injection, the distilled water for injection may possibly irritate the bladder more strongly than a physiological saline. For this reason, in order to reduce the pain from which the patient suffers at the time of injection, such an injectable is often dissolved in a physiological saline and used in a state that each injectable is thus made isotonic with the blood or body fluid. Nevertheless, it is known that the injectable of the anthracycline antineoplastic antibiotic is often formed like a cluster because π electron clouds thereof overlap with each other due to a substance such as a physiological saline carrying an electrical charge. Thus, it takes a longer time to dissolve such an injectable (see Document 1: Q&A of injection drug incompatibility, Jiho Inc., 2006, pp. 61-62).

For this reason, there have been attempted methods for improving the solubility of an anthracycline antineoplastic antibiotic in a physiological saline. For example, adding of an organic solvent such as ethanol at the time of preparing a pharmaceutical preparation is disclosed (see Document 2: Japanese Unexamined Patent Application Publication No. Hei 7-76515). However, such a method is not practiced yet because of a handling problem. Meanwhile, use of methyl p-hydroxybenzoate or the like (parabens) as a cosolubilizing agent with anthracycline glycoside is disclosed (see Document 3: Japanese Unexamined Patent Application Publication No. Sho 61-246129).

When used in an injection solution form, a drug needs to be dissolved in a predetermined solvent. However, drugs differ from each other in physiochemical property; accordingly, depending on the kind of solvent, a drug cannot be dissolved completely in many cases. For this reason, there have been various attempts to dissolve individual drugs by using a solubilizing aid so that the drugs can be rapidly dissolved in their given solvents.

However, even when a drug is successfully dissolved, it is known that the addition of the solubilizing aid, in turn, causes a so-called contraindication that the stability of the drug may be deteriorated, or the injectable may be colored or decomposed. Therefore, it is not easy to find out a specific solubilizing aid compatible with each drug.

For this reason, in order to improve the solubility of various injectables, the use of a solubilizing aid has been examined. For example, an aromatic carboxylic acid is used as a solubilizing aid for amythiamicin that is an anti-bacterial antibiotic (see Document 4: Japanese Unexamined Patent Application Publication No. Hei 9-124503). Moreover, a base such as sodium hydroxide is used as a solubilizing aid for loxoprofen sodium that is an anti-inflammatory drug (see Document 5: International Application Japanese-Phase Publication No. 2004-515526).

DISCLOSURE OF THE INVENTION

As to an injectable of an anthracycline antineoplastic antibiotic, it takes a significantly long time to completely dissolve the injectable in a physiological saline. Accordingly, such an injectable causes a considerable burden in operation for use by health care professionals. Additionally, when a physiological saline is unintentionally added, the injectable cannot be dissolved within a practical time frame. Consequently, the expensive injectable is wasted, not only causing a large economical loss, but also hindering the medical expense reduction promotion by the government. Thus, a development of an injectable is desired, which is capable of dissolving an anthracycline antineoplastic antibiotic readily and rapidly even in the presence of a physiological saline, and furthermore which does not induce an adverse effect such as a contraindication on the antibiotic.

The present inventors have earnestly studied to improve the solubility of an injectable of an anthracycline antineoplastic antibiotic in a physiological saline. Consequently, the inventors found out the following. Specifically, when a specific cyclic acid amide such as nicotinic acid amide, isonicotinic acid amide or gentisic acid ethanolamide is added as a solubilizing aid, it is made possible to dissolve the anthracycline antineoplastic antibiotic rapidly even in the presence of a physiological saline without inducing an adverse effect such as a contraindication on the antibiotic. Thus, the inventors have completed the present invention.

The present invention relates to the following inventions.

<1> An injectable comprising: an anthracycline antineoplastic antibiotic; and at least one acid amide selected from the group consisting of nicotinic acid amide, isonicotinic acid amide and gentisic acid ethanolamide.

<2> The injectable according to <1>, wherein the anthracycline antineoplastic antibiotic is at least one substance selected from the group consisting of aclarubicin hydrochloride, amrubicin hydrochloride, idarubicin hydrochloride, epirubicin hydrochloride, daunorubicin hydrochloride, doxorubicin hydrochloride, pirarubicin hydrochloride and mitoxantrone hydrochloride.

<3> The injectable according to <1>, wherein a content of the acid amide is 0.75 mg to 12.5 mg per mg (titer) of the anthracycline antineoplastic antibiotic.

<4> An injection solution comprising: an anthracycline antineoplastic antibiotic; at least one acid amide selected from the group consisting of nicotinic acid amide, isonicotinic acid amide and gentisic acid ethanolamide; and a dissolution solution.

<5> An injection kit preparation comprising: a freeze-dried injectable of an anthracycline antineoplastic antibiotic; and a dissolution solution containing at least one acid amide selected from the group consisting of nicotinic acid amide, isonicotinic acid amide and gentisic acid ethanolamide.

<6> An injection kit preparation comprising: a freeze-dried injectable of an anthracycline antineoplastic antibiotic; and a container filled with at least one acid amide selected from the group consisting of nicotinic acid amide, isonicotinic acid amide and gentisic acid ethanolamide.

In the present invention, a specific cyclic acid amide such as nicotinic acid amide, isonicotinic acid amide or gentisic acid ethanolamide is added as a solubilizing aid. Thereby, an anthracycline antineoplastic antibiotic is rapidly dissolved even in the presence of a physiological saline. This enables improvement in operation by healthcare professionals and treatment time efficiency. Furthermore, the present invention allows an improvement in the solubility without inducing an adverse effect such as a contraindication on the anthracycline antineoplastic antibiotic. Thereby, the stability of the injectable and the stability of the injection solution after the dissolution are sufficiently retained.

DETAILED DESCRIPTION OF THE PREFERRED EMBODIMENTS

First, an injectable and an injection solution of the present invention will be described.

The injectable of the present invention comprises: an anthracycline antineoplastic antibiotic; and at least one acid amide selected from the group consisting of nicotinic acid amide, isonicotinic acid amide and gentisic acid ethanolamide.

In addition, the injection solution of the present invention comprises: an anthracycline antineoplastic antibiotic; at least one acid amide selected from the group consisting of nicotinic acid amide, isonicotinic acid amide and gentisic acid ethanolamide; and a dissolution solution.

In the injectable and the injection solution of the present invention, at least one cyclic acid amide selected from the group consisting of nicotinic acid amide, isonicotinic acid amide and gentisic acid ethanolamide is blended. Adding such a specific cyclic acid amide as a solubilizing aid makes it possible to dissolve an anthracycline antineoplastic antibiotic rapidly even in the presence of a physiological saline without inducing an adverse effect such as a contraindication on the antibiotic.

In the injectable and the injection solution of the present invention, the amount of the specific acid amide is not particularly limited. However, from the viewpoint that health care professionals can feel a reduction in the operation burden owing to the improved solubility, the amount is preferably 0.75 mg or more, and more preferably 1.00 mg or more, per mg (titer) of the anthracycline antineoplastic antibiotic. Meanwhile, it is not particularly necessary to set the upper limit on the amount of the specific acid amide. However, in considering the previous usage examples also, the upper limit is preferably 12.5 mg or less per mg (titer) of the anthracycline antineoplastic antibiotic.

Examples of the anthracycline antineoplastic antibiotic used in the present invention include aclarubicin hydrochloride, amrubicin hydrochloride, idarubicin hydrochloride, epirubicin hydrochloride, daunorubicin hydrochloride, doxorubicin hydrochloride, pirarubicin hydrochloride, mitoxantrone hydrochloride, and the like. Above all, daunorubicin hydrochloride, doxorubicin hydrochloride, and pirarubicin hydrochloride are preferable.

A salt of the anthracycline antineoplastic antibiotic of the present invention is not particularly limited, as long as the salt is pharmaceutically acceptable. Preferably, it is possible to use hydrochloride, sulfate, nitrate, acetate, phosphate, benzoate, maleate, fumarate, succinate, hydrobromide, hydroiodide, tartrate, oxalate, citrate, aspartate, methanesulfonate, methanedisulfonate, ethanesulfonate, propanesulfonate, glyoxylate, benzenesulfonate, or the like.

A method of preparing the injectable of the present invention is not particularly limited, and an ordinary method can be adopted. As a general method, for example, an anthracycline antineoplastic antibiotic, an excipient and a specific acid amide described above are dissolved in distilled water for injection. The pH is adjusted with a pH adjuster. Thus, a dissolution solution is obtained. Next, this dissolution solution is aseptically filtered through a membrane filter, and a predetermined amount of the dissolution solution is distributed into a vial bottle and then freeze-dried. Thus, an injectable of the present invention can be prepared.

As the excipient, it is possible to add lactose, mannitol, sorbitol, dextran, glucose, or the like. Meanwhile, examples of the pH adjuster include hydrochloric acid, sodium hydroxide, and the like.

The container into which the dissolution solution is distributed is not limited to a vial bottle. It is also possible to use an ampule, a prefilled syringe, or the like.

In the injectable of the present invention, pharmaceutically acceptable additives that are normally used for an injectable can further be used to an extent that the object of the present invention is not impaired. Examples of such additives include a preservative, an analgesic, an antioxidant, and the like. Examples of the preservative include methyl parahydroxybenzoate, propyl parahydroxybenzoate, thimerosal, chlorobutanol, and the like. Examples of the analgesic include benzyl alcohol, mepivacaine hydrochloride, and xylocalne hydrochloride. Examples of the antioxidant include ascorbic acid, sodium hydrogensulfite, sodium sulfite, and the like.

A method of obtaining the injection solution of the present invention using the injectable of the present invention is not particularly limited, either, and an ordinary method can be adopted. As a general method, for example, the injectable of the present invention is dissolved in a dissolution solution when in use. Thus, an injection solution of the present invention can be obtained. Such a dissolution solution is not particularly limited, but distilled water for injection, a saline, a dextrose solution, or the like can be used suitably. Meanwhile, the amount of the dissolution solution may be adjusted as appropriate for use, depending on the concentration of the injection solution when used.

Next, an injection kit preparation of the present invention will be described.

A first injection kit preparation of the present invention comprises: a freeze-dried injectable of an anthracycline antineoplastic antibiotic; and a dissolution solution containing at least one acid amide selected from the group consisting of nicotinic acid amide, isonicotinic acid amide and gentisic acid ethanolamide.

In addition, a second injection kit preparation of the present invention comprises: a freeze-dried injectable of an anthracycline antineoplastic antibiotic; and a container filled with at least one acid amide selected from the group consisting of nicotinic acid amide, isonicotinic acid amide and gentisic acid ethanolamide.

The freeze-dried injectable of an anthracycline antineoplastic antibiotic used in the first and second injection kit preparations of the present invention may be the same as the aforementioned injectable of the present invention except that the specific acid amide is not included. For example, the freeze-dried injectable can be prepared by the same method as the aforementioned method of preparing the injectable of the present invention except that the specific acid amide is not added.

Meanwhile, the dissolution solution containing the specific acid amide used in the first injection kit preparation of the present invention is preferably an aqueous solution in which the specific acid amide is dissolved in distilled water for injection, a physiological saline, or the like. This dissolution solution can be used while being filled in a vial bottle, an ampule, a prefilled syringe, or the like.

Moreover, in the container filled with the above-described specific acid amide used in the second injection kit preparation of the present invention, it is preferable that the specific acid amide in a powder form be filled in a container used for an injectable such as a vial bottle, an ampule, a prefilled syringe, or the like. In this case, the container can be used while the specific acid amid is being dissolved in a dissolution solution such as distilled water for injection or a physiological saline when in use. Furthermore, in this case, pharmaceutically acceptable additives that are normally used for an injectable can be added also to an extent that the object of the present invention is not impaired.

The amount of the specific acid amide used in the first and second injection kit preparations of the present invention is not particularly limited. However, from the viewpoint that health care professionals can feel a reduction in the operation burden owing to the improved solubility, the amount is preferably 0.4 mg or more, and more preferably 1.0 mg or more, per mg (titer) of the anthracycline antineoplastic antibiotic. Meanwhile, the upper limit on the amount of the specific acid amide does not particularly have to be set. However, in considering the previous usage examples also, the upper limit is preferably 12.5 mg or less per mg (titer) of the anthracycline antineoplastic antibiotic.

EXAMPLES

Hereinbelow, the present invention will be more specifically described on the basis of Examples and Comparative Examples. However, the present invention is not limited to the following Examples.

Note that the following compounds were used.

Pirarubicin hydrochloride: prepared by adding 0.0014-mL hydrochloric acid with a concentration of 35% to 10 mg (titer) of pirarubicin (manufactured by Meiji Seika Kaisha, Ltd.).

Therarubicin for injection: generic name "pirarubicin", manufactured by Meiji Seika Kaisha, Ltd.

Daunorubicin: manufactured by Meiji Seika Kaisha, Ltd.

Idarubicin: manufactured by Pfizer Inc.

Doxorubicin: manufactured by Kyowa Hakko Kogyo Co., Ltd.

Epirubicin: manufactured by Pfizer Inc.

Aclarubicin: manufactured by Mercian Corporation

Nicotinic acid amide: manufactured by YUKI GOSEI KOGYO CO., LTD.

Isonicotinic acid amide: manufactured by Wako Pure Chemical Industries, Ltd.

Gentisic acid ethanolamide: manufactured by SEKISUI MEDICAL Co., Ltd. (former name: Daiichi Pure Chemical Co., Ltd.)

Nicotinic acid: manufactured by Wako Pure Chemical Industries, Ltd.

N,N'-dimethylacetamide: manufactured by Wako Pure Chemical Industries, Ltd.

Methyl parahydroxybenzoate: manufactured by Nacalai Tesque, Inc.

Urea: manufactured by JUNSEI CHEMICAL CO., LTD.

Polysorbate 20: manufactured by Nikko Chemicals Co., Ltd.

MACROGOL 4000: manufactured by NOF CORPORATION

Polyoxyethylene (160) polyoxypropylene (30) glycol: manufactured by BASF SE

Citric acid: manufactured by JUNSEI CHEMICAL CO., LTD.

Sodium edetate: manufactured by DOJINDO LABORATORIES.

Preparation Example 1

Preparation of Injectable with 20 mg of Nicotinic Acid Amide Blended 1.6 g (titer) of pirarubicin hydrochloride, 1.6 g of nicotinic acid amide and 14.4 g of lactose were dissolved in distilled water for injection. The pH was adjusted to 6 with 0.01 mol/L of a sodium hydroxide aqueous solution. Thus, a dissolution solution with a total amount of 240 mL was obtained. The dissolution solution was aseptically filtered and filled into vials each having a volume of 10 mL. Then, the solution was freeze-dried. After drying, each vial was capped with a rubber stopper. Thus, 80 injectables of the present invention were obtained.

Preparation Example 2

Preparation of Injectable with 80 mg of Nicotinic Acid Amide Blended 1.6 g (titer) of pirarubicin hydrochloride, 6.4 g of nicotinic acid amide and 14.4 g of lactose were dissolved in distilled water for injection. The pH was adjusted to 6 with 0.01 mol/L of a sodium hydroxide aqueous solution. Thus, a dissolution solution having a total amount of 240 mL was obtained. The dissolution solution was aseptically filtered and filled into vials each having a volume of 10 mL. Then, the solution was freeze-dried. After drying, each vial was capped with a rubber stopper. Thus, 80 injectables of the present invention were obtained.

Comparative Preparation Example 1

Preparation of Injectable without the Above-Described Specific Acid Amide Blended 1.6 g (titer) of pirarubicin hydrochloride and 14.4 g of lactose were dissolved in distilled water for injection. The pH was adjusted to 6 with 0.01 mol/L of a sodium hydroxide aqueous solution. Thus, a dissolution solution having a total amount of 240 mL was obtained. The dissolution solution was aseptically filtered and filled into vials each having a volume of 10 mL. Then, the solution was freeze-dried. After drying, each vial was capped with a rubber stopper. Thus, 80 injectables were obtained.

Test Example 1

Examples 1 to 3 and Comparative Examples 1 to 9

Solubility Test on Injectables with Various Solubilizing Aids Blended

Various types of solubilizing aids shown in Table 1 were each dissolved in 3 mL of distilled water for injection so as to be blended in a corresponding one of the amounts shown in the table. The solutions were each added to 20 mg of therarubicin for injection and completely dissolved. The solutions thus obtained were freeze-dried as in Preparation Example 1. Thus, injectables were prepared. Then, to each of the obtained injectables, 10 mL of a physiological saline was added and shaken. The solubility of the antibiotic was checked.

As a result, as shown in Table 1, with respect to the injectable in which nicotinic acid amide, isonicotinic acid amide, or gentisic acid ethanol amide was blended, the antibiotic was dissolved in the physiological saline in a short time. In contrast, with respect to the injectables in which the other respective solubilizing aids were blended, the antibiotics were not dissolved in the physiological salines in a short time. Note that the solubilizing aid was blended in an amount determined with the maximum amount in the previous usage examples taken into consideration.

TABLE 1

| Ex./Comp. Ex. | Solubilizing aid | Blended amount | Solubility |
|---|---|---|---|
| Ex. 1 | Nicotinic acid amide | 250 mg | Dissolved within 30 seconds |
| Ex. 2 | Isonicotinic acid amide | 250 mg | Dissolved within 60 seconds |
| Ex. 3 | Gentisic acid ethanol amide | 100 mg | Dissolved within 30 seconds |
| Comp. Ex. 1 | Nicotinic acid | 60 mg | Not dissolved within 10 minutes |
| Comp. Ex. 2 | N,N'-dimethylacetamide | 300 mg | Not dissolved within 10 minutes |
| Comp. Ex. 3 | Methyl parahydroxybenzoate | 2 mg | Not dissolved within 10 minutes |
| Comp. Ex. 4 | Urea | 50 mg | Not dissolved within 10 minutes |
| Comp. Ex. 5 | Polysorbate 20 | 80 mg | Not dissolved within 10 minutes |
| Comp. Ex. 6 | MACROGOL 4000 | 120 mg | Not dissolved within 10 minutes |
| Comp. Ex. 7 | Polyoxyethylene (160) polyoxypropylene (30) glycol | 10 mg | Not dissolved within 10 minutes |
| Comp. Ex. 8 | Citric acid | 0.4 mg | Not dissolved within 10 minutes |
| Comp. Ex. 9 | Sodium edetate | 1.7 mg | Not dissolved within 10 minutes |

Test Example 2

Examples 4 to 8 and Comparative Examples 10 to 14

Solubility Test on Various Anthracycline Antineoplastic Antibiotics

Various types of anthracycline antineoplastic antibiotics shown in Table 2 were each dissolved in 2 mL of distilled water for injection with 160 mg of nicotinic acid amide blended so as to be blended in a corresponding one of the amounts shown in the table. Each of the solutions thus obtained was freeze-dried as in Preparation Example 1. Thus, injectables were prepared (Examples 4 to 8). Additionally, injectables were prepared as in Examples 4 to 8 except that nicotinic acid amide was not blended. These injectables were designed as reference products (Comparative Examples 10 to 14). Then, to each of the obtained injectables, 3 mL of 10% saline was added. While the mixture was being shaken, the solubility of the antibiotic was checked every 30 seconds.

As a result, as shown in Table 2, with respect to the injectables in which no nicotinic acid amide was blended with the anthracycline antineoplastic antibiotic, the antibiotics were not dissolved in the salines at all. In contrast, with respect to the injectables in which nicotinic acid amide was blended, all of the antibiotics were dissolved in the salines in a short time. Note that the names of the antibiotics were listed by their generic names.

TABLE 2

| | Solubility | |
|---|---|---|
| Types of antibiotics | Reference product | Nicotinic acid amide-blended product |
| Daunorubicin, 20 mg (titer) | Not dissolved within 10 minutes (Comp. Ex. 10) | Dissolved within 30 seconds (Ex. 4) |
| Idarubicin, 5 mg (titer) | Not dissolved within 10 minutes (Comp. Ex. 11) | Dissolved within 30 seconds (Ex. 5) |
| Doxorubicin, 10 mg (titer) | Not dissolved within 10 minutes (Comp. Ex. 12) | Dissolved within 30 seconds (Ex. 6) |
| Epirubicin, 10 mg (titer) | Not dissolved within 10 minutes (Comp. Ex. 13) | Dissolved within 30 seconds (Ex. 7) |
| Aclarubicin 20 mg (titer) | Not dissolved within 10 minutes (Comp. Ex. 14) | Dissolved within 60 seconds (Ex. 8) |

Test Example 3

Examples 9 to 11 and Comparative Example 15

Solubility Test on Injectables with Different Amounts of Nicotinic Acid Amide Blended Injectables (Examples 9 to 11 and Comparative Example 15) with different amounts of nicotinic acid amide added as shown in Table 3 were prepared by the same method as that in Preparation Example 1. Then, to each of the obtained injectables, 10 mL of a physiological saline was added, and the vial was shaken. The dissolution state of the antibiotic was checked over time, and a period of time required until the antibiotic was completely dissolved was measured.

As a result, as shown in Table 3, with respect to the reference product injectable in which no nicotinic acid amide was added, it took 10 minutes or longer for the antibiotic to be completely dissolved, and the measurement was terminated in mid-course. Meanwhile, with respect to the injectables with the amount of nicotinic acid amide added being 20 mg or more, the antibiotics were rapidly dissolved. Moreover, it was found out that the larger the amount of nicotinic acid amide added, the shorter the dissolution time, and that, when the added amount was 20 mg or more, the solubility was sharply improved, and thus the dissolution was rapidly promoted.

TABLE 3

|  | Comp. Ex. 15 (Reference product) | Ex. 9 (Formulation 1) | Ex. 10 (Formulation 2) | Ex. 11 (Formulation 3) |
| --- | --- | --- | --- | --- |
| Pirarubicin hydrochloride | 20 mg (titer) | 20 mg (titer) | 20 mg (titer) | 20 mg (titer) |
| Nicotinic acid amide | — | 15 mg | 20 mg | 80 mg |
| Lactose | 180 mg | 180 mg | 180 mg | 180 mg |
| Sodium hydroxide | Adequate amount | Adequate amount | Adequate amount | Adequate amount |
| Distilled water for injection | Amount such that total amount was 3 mL | Amount such that total amount was 3 mL | Amount such that total amount was 3 mL | Amount such that total amount was 3 mL |
| Dissolution time | 10 minutes or longer | 8 minutes 10 seconds | 10 seconds | 5 seconds |

Test Example 4

Example 12 and Comparative Example 16

Stress Tests on Injectables

The injectable (containing 20 mg of nicotinic acid amide) prepared in Preparation Example 1 was used and left under the temperature condition of 40° C. The percentage of pirarubicin remaining after the elapse of the storage duration shown in Table 4 was measured. Note that the injectable prepared in Comparative Preparation Example 1 without nicotinic acid amide blended was used as a reference product, and the percentage of remaining pirarubicin was measured in the same way.

As a result, as shown in Table 4, the injectable prepared in Preparation Example 1 showed the stability (percentage of remaining pirarubicin) equivalent to that of the reference product not containing nicotinic acid amide. In other words, it was found out that, even if nicotinic acid amide is blended, no adverse effect such as a contraindication is induced on pirarubicin that is the main component.

TABLE 4

| Storage condition | Comp. Ex. 16 (Reference product) Remaining pirarubicin percentage (%) | Ex. 12 (injectable of Preparation Example 1) Remaining pirarubicin percentage (%) |
| --- | --- | --- |
| Before test | — | — |
| 40° C., 2 weeks | 98.2 | 98.4 |
| 40° C., 1 month | 97.5 | 97.7 |
| 40° C., 2 months | 96.0 | 97.1 |

Test Example 5

Examples 13 to 17 and Comparative Example 17

Solubility Test with Dissolution Solution of Nicotinic Acid Amide

To 20 mg (titer) of therarubicin for injection, 10 mL of the dissolution solution in which nicotinic acid amide was dissolved in a physiological saline was added so as to be blended in a corresponding one of the amounts shown in Table 5. The mixture was shaken. The solubility of the antibiotic was then checked every 30 seconds.

As a result, as shown in Table 5, it was found out that the addition of nicotinic acid amide allows pirarubicin to be dissolved in a physiological saline. Accordingly, it was found out that the addition of nicotinic acid amide in the form of a dissolution solution allows pirarubicin, i.e. an anthracycline antineoplastic antibiotic, to be dissolved, and also allows pirarubicin to be dissolved even when a physiological saline also exists.

TABLE 5

| Ex./Comp. Ex. | Amount of nicotinic acid amide added (mg) | Dissolution time |
| --- | --- | --- |
| Comp. Ex. 17 | Not added | 10 minutes or longer |
| Ex. 13 | 8 | 120 seconds |
| Ex. 14 | 15 | 120 seconds |
| Ex. 15 | 20 | 60 seconds |
| Ex. 16 | 80 | within 30 seconds |
| Ex. 17 | 250 | within 30 seconds |

INDUSTRIAL APPLICABILITY

The present invention makes it possible to dissolve an anthracycline antineoplastic antibiotic rapidly even in the presence of a physiological saline without inducing an adverse effect such as a contraindication on the antibiotic. Therefore, the present invention is very useful as a technology to provide an injectable and an injection solution each comprising an anthracycline antineoplastic antibiotic.

The invention claimed is:

1. An injectable composition comprising:
   an anthracycline antineoplastic antibiotic; and
   at least one acid amide selected from the group consisting of nicotinic acid amide, isonicotinic acid amide and gentisic acid ethanolamide in an amount sufficient to dissolve the antibiotic in a dissolution solution faster than if the acid amide were not present.

2. The injectable composition according to claim 1, wherein the anthracycline antineoplastic antibiotic is at least one substance selected from the group consisting of aclarubicin hydrochloride, amrubicin hydrochloride, idarubicin hydrochloride, epirubicin hydrochloride, daunorubicin hydrochloride, doxorubicin hydrochloride, pirarubicin hydrochloride and mitoxantrone hydrochloride.

3. The injectable composition according to claim 1, wherein a content of the acid amide is 0.75 mg to 12.5 mg per mg (titer) of the anthracycline antineoplastic antibiotic.

4. An injection solution comprising:
   an anthracycline antineoplastic antibiotic;
   at least one acid amide selected from the group consisting of nicotinic acid amide, isonicotinic acid amide and gentisic acid ethanolamide in an amount sufficient to dissolve the antibiotic in a dissolution solution faster than if the acid amide were not present; and
   the dissolution solution.

5. An injection kit preparation comprising:
   a freeze-dried injectable of an anthracycline antineoplastic antibiotic; and
   a dissolution solution containing at least one acid amide selected from the group consisting of nicotinic acid amide, isonicotinic acid amide and gentisic acid ethanolamide in an amount sufficient to dissolve the antibiotic in the dissolution solution faster than if the acid amide were not present.

6. An injection kit preparation comprising:
a freeze-dried injectable of an anthracycline antineoplastic antibiotic; and
a container filled with at least one acid amide selected from the group consisting of nicotinic acid amide, isonicotinic acid amide and gentisic acid ethanolamide in an amount sufficient to dissolve the antibiotic in a dissolution solution faster than if the acid amide were not present.

* * * * *